United States Patent [19]

Klein

[11] Patent Number: 4,784,136

[45] Date of Patent: Nov. 15, 1988

[54] ELECTRICAL EPILATION

[76] Inventor: Peter Klein, 19763 - 44th Avenue, Langley, British Columbia, Canada

[21] Appl. No.: 2,421

[22] Filed: Jan. 12, 1987

[51] Int. Cl.$^4$ .............................................. A61B 17/41
[52] U.S. Cl. ............................ 128/303.13; 128/303.17
[58] Field of Search ...................... 128/303.13, 303.18, 128/303.19, 355

[56] References Cited

U.S. PATENT DOCUMENTS

| 2,894,512 | 7/1959 | Tapper | 128/303.18 |
| 3,054,405 | 9/1962 | Tapper | 128/303.18 |
| 4,041,952 | 8/1977 | Morrison, Jr. et al. | 128/303.13 |
| 4,174,714 | 11/1979 | Mehl | 128/303.13 |
| 4,295,467 | 10/1981 | Mann et al. | 128/303.18 |

Primary Examiner—Lee S. Cohen
Attorney, Agent, or Firm—Fetherstonhaugh & Co.

[57] ABSTRACT

In electrical epilation equipment useful to permanently remove unwanted body hair it is known to have a needle electrode to affect the immediate surroundings of the papilla. In this invention the needle electrode has been adapted to fit into the first arm of a pair of tweezers where its position can be adjusted so that the needle protrudes more or less from the tip of the tweezers first arm. This feature facilitates a consistent insertion depth of the needle into the follicles. Switches adapted to fit into the tweezers control electricity flow to the needle electrode when the tweezers is being closed to grip a hair. An indicator light adapted to fit into the tweezers monitors the presence of electrical energy at the needle electrode.

8 Claims, 3 Drawing Sheets

ELECTRICAL EPILATION

The invention relates to electrical epilation equipment which is used to permanently remove body hair. The equipment comprises a hand held epilation instrument with a needle electrode and a radio frequency generator or a DC current generator or a blend of radio frequency and DC current generator.

DESCRIPTION OF THE PRIOR ART

Such systems are well known in hair removal therapy and have been in use since many years. One system for instance is described in U.S. Pat. No. 2,444,173.

The characteristical needle electrode is used to affect the vicinity of the hair root by means of electrical currents. Depending on the kind of current, DC or RF, the effect is either of electrolytical or heat nature or a combination of both. Hereby one takes advantage of the fact that the electrical field strength gains a maximum at the tip of an electrode which is shaped like a needle. As the electrical field strength decreases rapidly with the distance from the needle tip so do the effects like electolytic action or heat. It is therefore necessary for the therapist to insert the needle electrode precisely into the follicle and accurately so deep, that the tip of the needle electrode is closest to the papilla. Without suitable technical means to support this difficult action of the therapist, his or her work becomes not only tiring from the high concentration level continuously required but the efficacy of the treatment becomes doubtful if the needle is inserted too deep or overtreatment of the skin can occur, leaving burning marks on it's surface.

After the papilla of one hair has been sufficiently treated with the electrical currents the needle electrode is retracted from the follicle and a pair of tweezers is used to pull the hair out. It is ergonomically unfavourable if the therapist must constantly switch between the needle electrode and the tweezers. The therapist's attention is deflected at least for a moment from the treated hair and it can easily happen that an untreated hair is pulled out which will regrow fast.

SUMMARY OF INVENTION

The invention seeks to provide an electro mechnical instrument for the permanent removal of body hair. This instrument works in conjunction with suitable electricity generators. The instrument combines the characteristics of traditionally separate tools like needle electrode, tweezers, switch and treatment indicator into one integral ergonomics oriented piece of equipment.

Accordingly the invention is in an electrical epilation equipment useful to permanently remove unwanted body hair including an electricity generator and a hand held epilation instrument, and is the improvement whereby the epilation instrument comprises: an electrically isolated pair of tweezers; a needle electrode adapted to fit into the first arm of the tweezers with means to adjust the length of the needle protruding from the tip of the tweezers first arm; switching devices fitted into the tweezers arms to control the electricity flow to the needle electrode; an indicator device, preferably a small light source, fitted into one of the tweezers arms to indicate when electrical energy is available at the needle electrode; and the electricity generator which is electrically connected to the hand held epilation instrument comprises: an electric power source of high frequency type or of direct current type or a blend of both; and means to control the flow of energy from the power source to the needle electrode whereby these means may consist of electrical circuits controlled by the switch action in the hand held epilation instrument to adjust the strength of the power source or to adjust the duration of the power available at the needle electrode.

Preferably the switch action is mechanically coupled with the position of the tweezers arms to each other, so that the switching action occurs shortly before the tweezers is closed.

The means to adjust the length of the needle electrode protruding from the tip of the tweezers first arm comprises: an electrically conductive support plate to which the needle electrode is bonded; a screw stud affixed to the support plate; a lock nut fitting the thread of the screw stud with an electrically isolated knob, whereby the diameter of the knob is bigger than the width of the slot described below; a longitudinally extended groove at the inside of the tweezers first arm in which the support plate can slide longitudinally; a slot of at least the length which is considered the maximum protrusion of the needle electrode from the tip of the first tweezers arm, whereby the slot runs in the centre line of the first tweezers arm and is intended to provide for screwing the lock nut to the screw stud with the knob against the outside of the tweezers first arm, so that tightening the lock nut results in increased friction of the support plate in the groove to secure the position of the support plate.

The switching devices in a preferred embodiment are two contact pins which are arranged at the inside of the tweezers second arm opposite to the support plate in the tweezers first arm, whereby the location of the contact pin is such that for every working position of the support plate the pair of contacts gets bridged by the support plate when the tweezers arms come close to each other.

Preferably a three conductor cable connects the two contact pins and one lead of the indicator light with the electricity generator, the other lead of the indicator light being connected to one of the contact pins, forming three electric circuits with separate current loops whereby the first circuit is to control the energy flow from the power source, the second circuit is for the treatment current, and the third circuit is to indicate the availability of energy for the treatment at the needle electrode.

BRIEF DESCRIPTION OF THE DRAWINGS

An embodiment of the invention is illustrated in the drawings, in which.

DESCRIPTION OF THE PREFERRED EMBODIMENT

Figure 1:
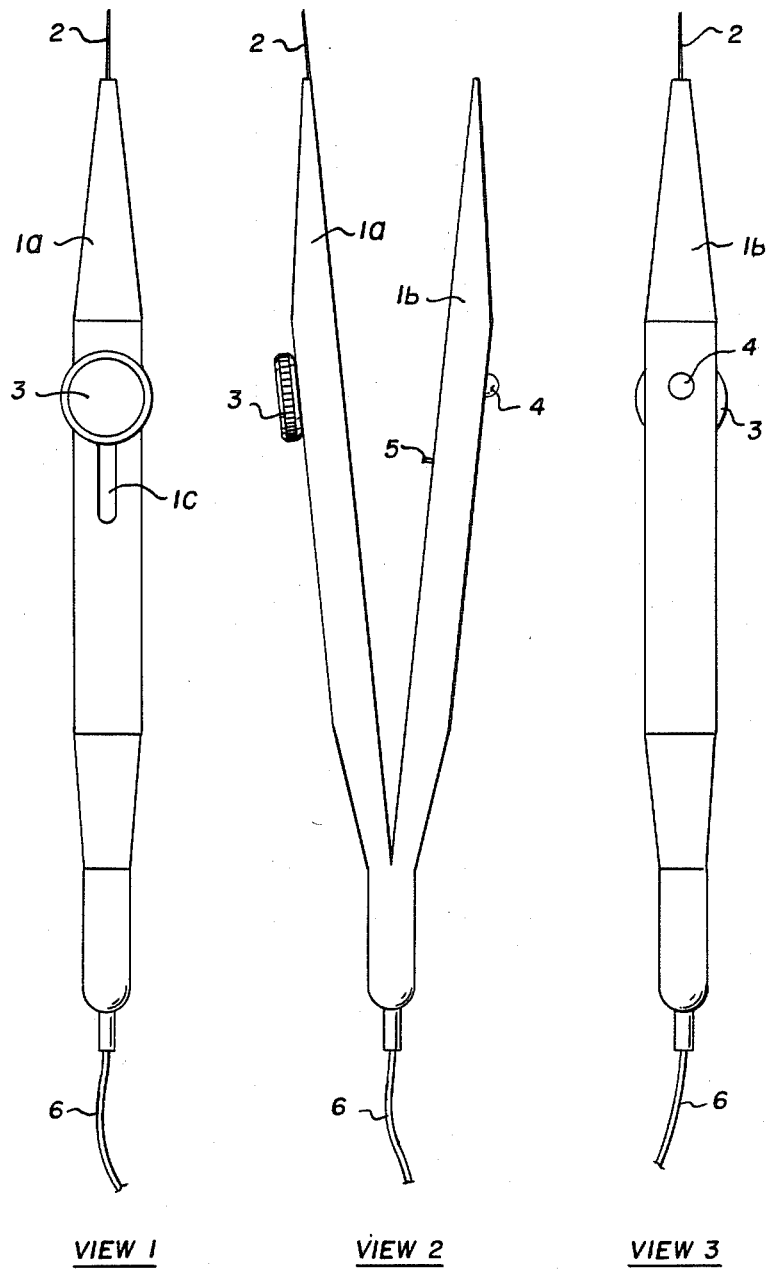
FIG. 1 shows the epilation instrument whereby
View 1 is a bottom view;
View 2 is a side view;
View 3 is a top view.

FIG. 1 view 2 shows the instrument with the tweezers arms 1a and 1b in there normally open position. The tweezers arms 1a and 1b are firmly attached to each other in the rear section and have sufficient elasticity to easily return to their normally open position when released from their closed position. The tweezers arms 1a and 1b are either of non conductive material or isolated against any electricity conducting parts inside.

The needle 2, which preferably is of stainless steel, protrudes from the tweezers arm 1a and is shown in its most protruding state.

Loosening lock nut 3 enables the operator to slide the needle 2 longitudinally within the limits given by slot 1c between the fully extended position and a position where the needle is fully retracted into the tweezers arm 1a.

The light emitter 4, preferably a diode, is visible for the operator on the surface of tweezers arm 1b.

A pair of contact pins, 5 arranged in a line perpendicular to the longitudinal axis of the instrument, protrudes from the inside of tweezers arm 1b.

Figure 2:
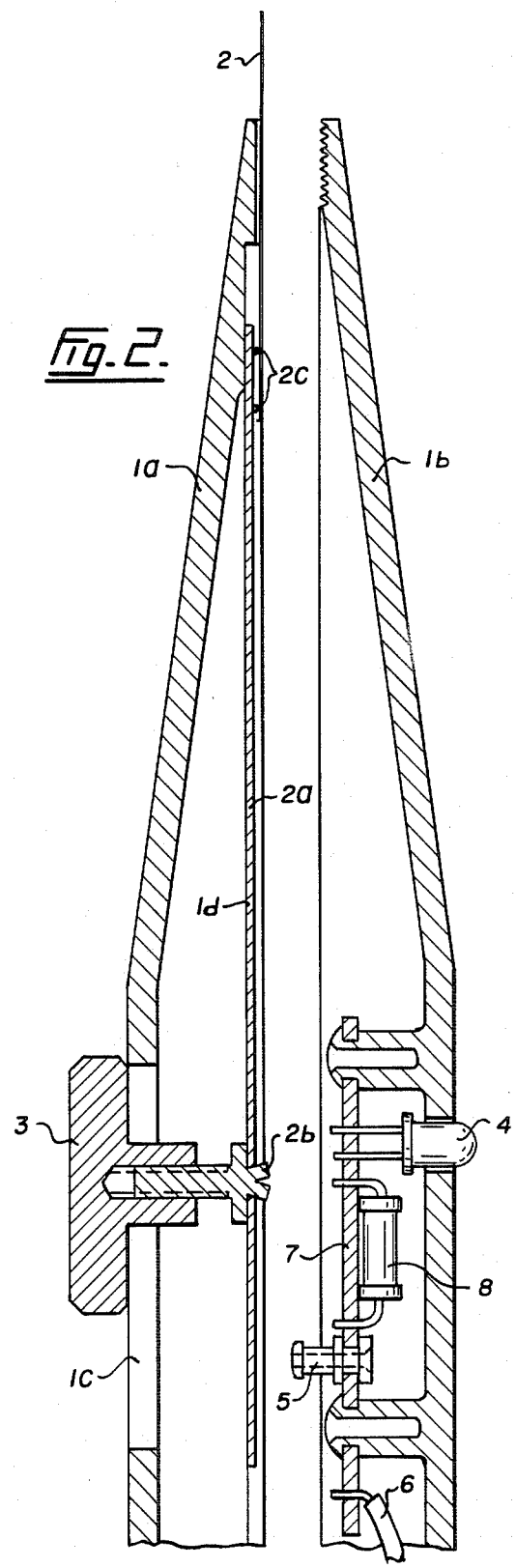
FIG. 2 is an enlarged section of the front part of the instrument with the tweezers arms shown in an almost closed position.

FIG. 2 shows in an enlarged section the front part of the tweezers arms 1a and 1b of the instrument.

The needle 2 is attached in electrically conductive manner, e.g. by weld spots 2c, to the needle support plate 2a. The needle support plate 2a is of conductive material, preferably metal. Together with the screw stud 2b and the needle 2 the needle support plate 2a forms one unit which can be removed from the instrument after lock nut 3 has been totally screwed off. This unit then can be easily be replaced by a spare one.

The lock nut 3 which on one end is shaped into a knurled knob, which diameter is bigger than the width of the instrument, is guided in slot 1c of tweezer arm 1a.

The needle support plate 2a rests on the shoulder of the longitudinally extended groove 1d. When lock nut 3 is tightened, the knurled knob is pressed against the outer surface of tweezer arm 1a and the needle carrier plate 2a is pressed against the shoulder of groove 1d. This causes the friction to lock the needle carrier plate 2a and therefore the needle 2 in position.

A printed circuit board 7 carrying the light emitting diode 4 and electrical components such as resistor 8 and contact pins 5 and cable 6 rests in a cavity of tweezer arm 1b.

Contact between the contact pins 5 and the needle carrier plate 2a is made shortly before the tweezer arms 1a and 1b touch each other. This is the case for instance when a hair is being gripped.

Figure 3:
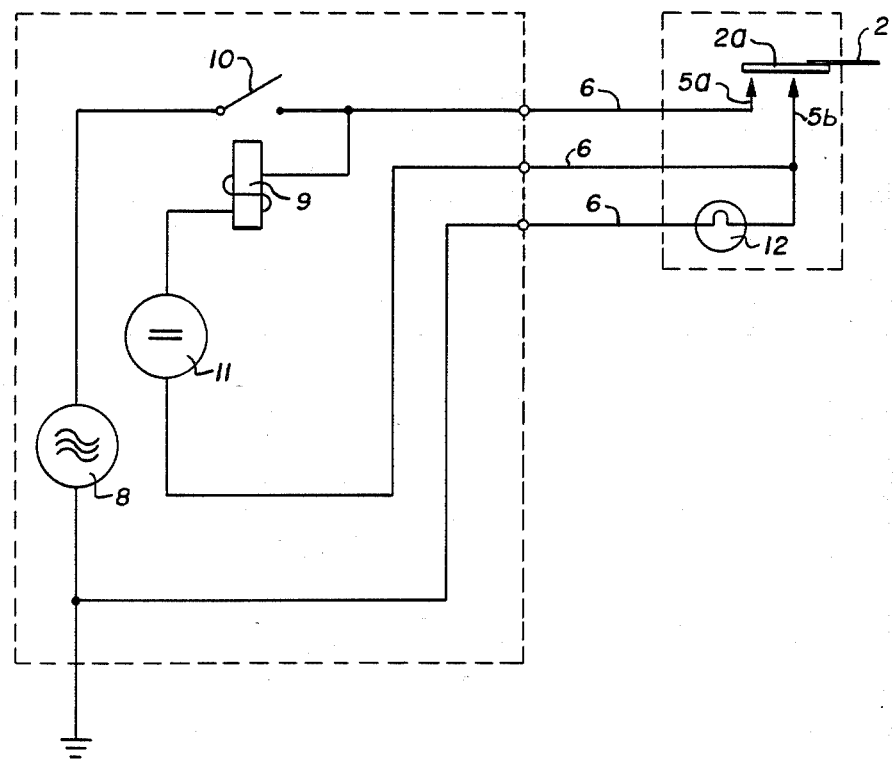
FIG. 3 shows in a simplified electrical circuit the interconnection between the elctricity generator and the epilation instrument.

FIG. 3 shows in a simplified schematic the principle functional relationship between the epilation instrument shown with needle 2 on the support plate 2a, contact pins 5a and 5b, the lamp 12 and cable 6 and the electricity generator shown with an RF power source 8, a DC power supply 11 and a relay contact 10 actuated by relay coil 9.

After the needle 2 has been inserted into a hair follicle the tweezers is closed to grip the hair by which action the needle support plate 2a gets in contact with contact pins 5a and 5b. This closes the DC circuit, particularly DC power supply 11 via relay coil 9, contact 5a, contact 5b and back to DC power supply 11. Contact 10, now being closed by relay 9, enables flow of the RF power via contact pin 5a and the needle support plate 2a to the tip of needle 2. The electrical field strength around the tip of needle 2 causes high current flow through the moist tissue at the papilla which heats up this immediate area so much, that the blood supply of the papilla can be dried out. The presence of high frequency power at the needle is indicated by lamp 12 with RF energy flow from RF generator 8, via contact 10, contact pin 5a, needle support plate 2a, contact pin 5b, lamp 12 and back to RF generator 8.

The very ergonomical handling of the instrument as well as the improved accuracy of the treatment should be noted. To adjust the correct needle length it is only necessary to grip one sample hair in the area which is to be treated with the instrument, so that the tweezer tips touch the skin. This is done with the needle fully retracted. When this hair is pulled out and still held with the instrument, the needle can be slid out so far that the visible length of the needle and the visible length of the hair match each other. It is considered a general rule that hair of the same type in the same treatment area grow out from the same depth in the epidermis.

With the needle locked in the found position, treatment of the rest of the hair follows the scheme of inserting the needle into a follicle until the tweezers tip touches the skin surface, closing the tweezers which automatically triggers the electrical action, and pulling the hair out. The electrical action can be monitored by means of the indicator light. It is therefore ensured that no untreated is pulled out. The therapist does not have to constantly switch between the earlier separate instrument of needle electrode and tweezers. The insertion depth of the needle is measured and not guessed any more.

The embodiments of the invention in which an exclusive property or privilege is claimed are defined as follows:

1. An electrical epilation apparatus for permanently removing unwanted body hair, comprising:
   an electrically isolated pair of tweezers having opposed first and second arms;
   a needle electrode bonded to an electrically conductive support plate slidably received in said first arm of said tweezers, said support plate having means to adjust the length of the needle electrode protruding from the tip of said first arm;
   switching means between said first and second arms of said tweezers adapted to control electricity flow to said needle electrode when said tweezer arms are closed and opened;
   an indicator light fitted into one of the tweezer arms and electrically connected to said switching means to indicate that said needle electrode is being energized; and
   electrical generator means adapted to supply electrical energy to said needle electrode when said tweezer arms are closed.

2. An apparatus as defined in claim 1 wherein said electrical generator means is connected between said switching means and said indicator light.

3. An apparatus as defined in claim 2 wherein said electrical generator means comprises an RF type power source.

4. An apparatus as defined in claim 2 wherein said electrical generator means comprises a DC type power source.

5. An apparatus as defined in claim 2 wherein said adjusting means comprises a screw stud affixed to said support plate, an electrically isolated knob, a lock nut attached to said knob to receive said screw stud, a slot extending longitudinally along said first arm, said screw stud being received in said slot so as to permit the distance said needle electrode protrudes from the tip of said first arm to be adjusted to a predetermined length.

6. An apparatus as defined in claim 5 wherein said adjusting means further comprises an interior groove extending longitudinally of said first arm, said support plate being slidably received in said interior groove.

7. An apparatus as defined in claim 6 wherein said switching means comprises first and second contact pins disposed on said second arm and adapted make contact with said support plate to energize said needle electrode when said tweezer arms approach one another.

8. An apparatus as defined in claim 7 wherein said electrical generator means comprises an RF generator connected between said first contact pin, a relay switch and said indicator light, and a DC power source connected between said first contact pin, a relay and said second contact pin.

* * * * *